United States Patent
Iordanov et al.

(10) Patent No.: US 9,918,904 B2
(45) Date of Patent: Mar. 20, 2018

(54) DRUG DELIVERY CAPSULES WITH EXTERNAL INTELLIGENCE

(71) Applicant: Medimetrics Personalized Drug Delivery, Briarcliff Manor, NY (US)

(72) Inventors: Ventzeslav Petrov Iordanov, Valkenswaard (NL); Hans Zou, Chappaqua, NY (US); Christoph Wanke, EW Veldhoven (NL); Klaas Kerkhop, Nuenen (NL); Jeffrey A. Shimizu, Cortlandt Manor, NY (US)

(73) Assignee: Stoco 10 GmbH, Heilbronn (DE)

( * ) Notice: Subject to any disclaimer, the term of this patent is extended or adjusted under 35 U.S.C. 154(b) by 17 days.

(21) Appl. No.: 14/434,548

(22) PCT Filed: Sep. 23, 2013

(86) PCT No.: PCT/US2013/061202
§ 371 (c)(1),
(2) Date: Apr. 9, 2015

(87) PCT Pub. No.: WO2014/058605
PCT Pub. Date: Apr. 17, 2014

(65) Prior Publication Data
US 2015/0272830 A1    Oct. 1, 2015

Related U.S. Application Data

(60) Provisional application No. 61/711,627, filed on Oct. 9, 2012.

(51) Int. Cl.
*A61J 7/00* (2006.01)
*A61J 7/04* (2006.01)
(Continued)

(52) U.S. Cl.
CPC .......... *A61J 7/0076* (2013.01); *A61J 7/0481* (2013.01); *A61M 31/002* (2013.01);
(Continued)

(58) Field of Classification Search
CPC ...... A61J 7/0076; A61J 7/0481; A61J 7/0418; A61J 7/0427; A61J 2200/70;
(Continued)

(56) References Cited

U.S. PATENT DOCUMENTS 4,731,765 A * 3/1988 Cole .................. A61J 7/04
206/534
4,844,076 A * 7/1989 Lesho .................. A01K 11/007
128/903

(Continued)

FOREIGN PATENT DOCUMENTS

WO    WO2008064428    6/2008
WO    WO 2011114332 A1 * 9/2011 ............ A61B 5/065

OTHER PUBLICATIONS

PCT Search Report dated Dec. 18, 2013 for PCT application No. PCT/US13/61202, 12 pages.
(Continued)

*Primary Examiner* — Nathan R Price
*Assistant Examiner* — Courtney Fredrickson
(74) *Attorney, Agent, or Firm* — Roger D. Emerson; Emerson Thomas Bennett

(57) ABSTRACT

A system for administering a medicament includes a plurality of capsules, a capsule dispenser, and a capsule activator. Each of the capsules includes a reservoir containing a medicament and an outlet in communication with the reservoir through which the medicament exits the capsule. The capsule dispenser releasably contains the ingestible capsules and is adapted to dispense the capsules to a user in accordance with a predetermined schedule. The capsule activator (Continued)

activates the dispensed capsules prior to administration to the user.

27 Claims, 3 Drawing Sheets

(51) Int. Cl.
| | |
|---|---|
| *A61M 31/00* | (2006.01) |
| *G06F 19/00* | (2018.01) |
| *B65D 83/04* | (2006.01) |
| *A61K 9/20* | (2006.01) |
| *A61K 51/12* | (2006.01) |
| *A61B 5/07* | (2006.01) |
| *A61B 5/00* | (2006.01) |

(52) U.S. Cl.
CPC ......... *G06F 19/3462* (2013.01); *A61B 5/073* (2013.01); *A61B 5/6861* (2013.01); *A61B 2560/0266* (2013.01); *A61B 2562/162* (2013.01); *A61J 7/0418* (2015.05); *A61J 7/0427* (2015.05); *A61J 2200/70* (2013.01); *A61K 9/20* (2013.01); *A61K 51/1258* (2013.01); *B65D 83/04* (2013.01); *B65D 83/0409* (2013.01)

(58) Field of Classification Search
CPC . A61M 31/002; A61M 31/00; G06F 19/3462; A61B 5/6861; A61B 2560/0266; A61B 5/073; A61B 1/00011; A61B 1/00032; B65D 83/04; B65D 83/0409; A61K 9/20; A61K 51/1258
See application file for complete search history.

(56) References Cited

U.S. PATENT DOCUMENTS

| | | | |
|---|---|---|---|
| 5,217,449 A | * | 6/1993 | Yuda ................ A61B 1/00027 604/131 |
| 5,860,957 A | | 1/1999 | Jacobsen et al. |
| 2005/0147559 A1 | | 7/2005 | von Alten |
| 2007/0213659 A1 | | 9/2007 | Trovato et al. |
| 2009/0275923 A1 | | 11/2009 | Shimizu et al. |
| 2010/0049012 A1 | | 2/2010 | Dijksman et al. |
| 2011/0166700 A1 | | 7/2011 | Dunn |
| 2013/0172694 A1 | * | 7/2013 | Zou ........................ A61B 5/07 600/302 |

OTHER PUBLICATIONS

Extended European Search Report dated May 25, 2016 for European Patent Application No. 13846079.5, 7 pages.

* cited by examiner

DRUG DELIVERY CAPSULES WITH EXTERNAL INTELLIGENCE

CROSS REFERENCE TO RELATED APPLICATION

This Application is a 35 U.S.C. 371 National Stage Entry of and claims priority to PCT Application No. PCT/US2013/061202 entitled "Drug Delivery Capsules With External Intelligence" filed on Sep. 23, 2013, which claims priority to U.S. Provisional Patent Application No. 61/711,627 filed on Oct. 9, 2012, entitled "Drug Delivery Capsules With External Intelligence," both of which are hereby incorporated by reference in their entirety.

BACKGROUND OF THE INVENTION

Technical Field

This invention relates to the administration of medicaments. More specifically, the invention relates to a smart capsule system for delivery of drugs or other materials to a user.

Description of Related Art

Drug dispensing apparatus and methods have been proposed in which a drug is contained in an enclosed ingestible or insertable capsule. An actuator and controls are also disposed in the capsule, to dispense the drug from the capsule at some specified time or upon a specified event. To date, engineered capsules with mechanical or electronic dispensing and sensing components have been proposed and studied that may be effective at releasing a drug or other medicament at a specified position along the alimentary canal. These controlled released capsules have been proposed in many number of ways, but all are similar in that they tend to be quite complex. The complexity results in a very high cost of manufacture and assembly, and uses to date have generally been limited to research and development. However, the controlled release of these capsules would be extremely beneficial in everyday usage for treating maladies of the alimentary canal, or even more broadly for dispensing any type of medication within a body cavity, such as at a desired position along the alimentary canal. However, as noted above, the cost associated with the complexity makes this impractical.

Accordingly, there is a need in the art for a low cost electronic capsule that could be used to dispense drugs intended to be taken at some determined time or interval.

Another drawback associated with conventional drug delivery systems, is that the user may administer as many doses as he desires, and in whatever interval they see fit. This is true even if the self-administered dosaging does not comport with recommended amounts. This can lead to ineffective treatment, and in some extreme examples, overdosing or unintended dependency.

Thus, there also is a need in the art for a medicament delivery system in which dosing of drugs is recorded and allowed only at specific times.

SUMMARY OF THE INVENTION

The present invention addresses the foregoing needs in the art by providing a medicament delivery system and methods that include a low-cost, controllable capsule, usable in any number of applications, including daily, generally low cost drug delivery.

In one aspect of the invention, a system for administering a medicament includes a plurality of capsules, a capsule dispenser, and a capsule activator. Each of the capsules includes a reservoir containing a medicament and an outlet in communication with the reservoir through which the medicament exits the capsule. The capsule dispenser releasably contains the ingestible capsules and is adapted to dispense the capsules to a user in accordance with a predetermined schedule. The capsule activator activates the dispensed capsules prior to administration to the user.

In another aspect of the invention, a method of administering a medicament to a user includes storing a plurality of capsules in a storage unit, dispensing at least one of the capsules from the storage unit to a user, activating the capsules prior to their administration to the user, and releasing the medicament from the reservoir after administration of the capsule to the user.

These and other features, aspects and embodiments of the invention will be better understood with reference to the appended drawing figures and following detailed description of the invention in which preferred embodiments of the invention are shown and described.

BRIEF DESCRIPTION OF THE DRAWING FIGURES

DETAILED DESCRIPTION OF THE INVENTION

As noted above, the present disclosure relates to medicament delivery and more particularly to systems and methods for administering a medicament to a patient. The term medicament is used herein to mean any substance that can be administered to a user via a capsule. Medicaments include, but are not limited to, pharmaceutically active compounds, drugs, dyes, radio-labeled markers, vaccines, physiological markers, and diagnostic agents.

The systems and methods of the disclosure are preferably more economical and robust than existing systems employing engineered drug delivery capsules, while still providing the flexibility, reporting functionality and control offered by existing electronic capsules. Preferred embodiments of the present invention generally provide drug delivery capsules with external intelligence.

Figure 1:
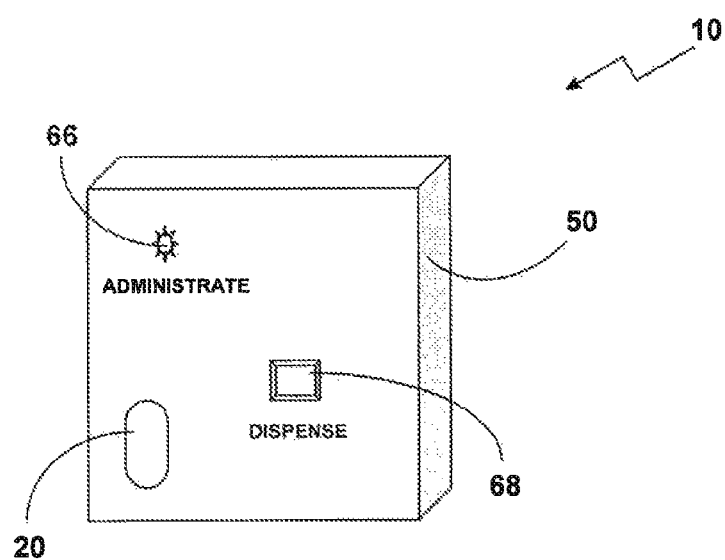
FIG. 1 is a schematic illustration of a medicament administration system according to an embodiment of the invention.

FIG. 1 shows a first embodiment of the invention, including a medicament delivery system 10 having an electronic capsule 20 and an external device 50. The external device 50 is so termed only because, unlike the capsule 20, it is not intended for administration to the user, e.g., by ingestion or insertion. The many features and functionalities of the capsule 20 and the device 50 will be described in more detail, as follows.

Figure 2:
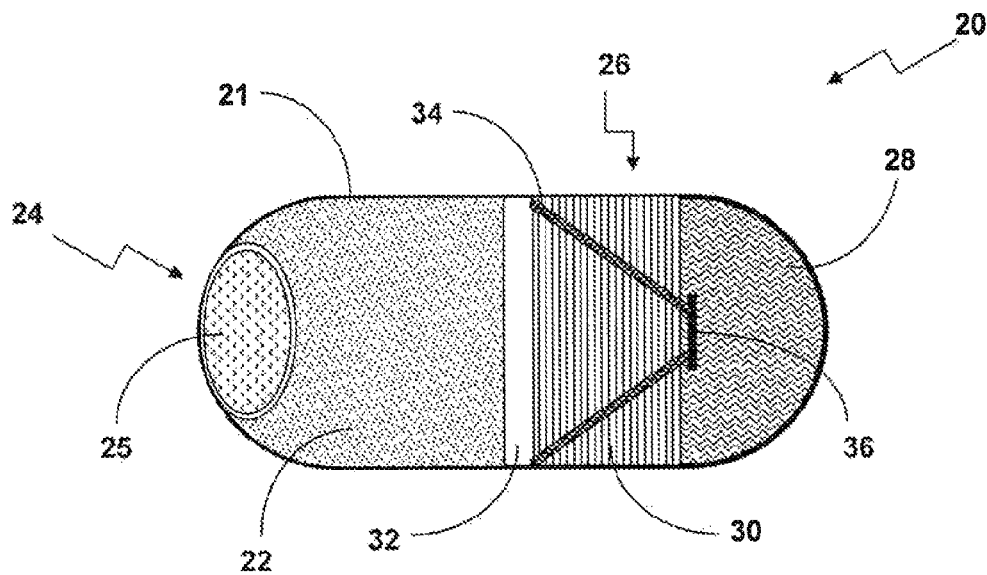
FIG. 2 is a section view of a capsule used in the system illustrated in FIG. 1.

An embodiment of the capsule 20 is illustrated in FIG. 2. The capsule 20 is sized for ingestion by or insertion into a user. It preferably includes a reservoir 22 for storing a medicament (not shown) to be administered to the user, an outlet 24 through which the medicament is dispensed from the reservoir 22, an actuator 26 for aiding in dispensing of the medicament, and controls 28. The reservoir is initially closed, and in some embodiments sealed, such as by a cap 25 covering the outlet 24 to separate the medicament from the environment. In alternative embodiments, some of which will be discussed below, additional features and components may be included in the capsule, but their inclusion may operate to increase the cost of the capsule. As noted above, in some embodiments of the invention the cost of the capsule is kept as low as possible, as the capsule 20 is the disposable piece in the system 10 and keeping the cost of the capsule down will enable the system to be used in a broader range of medicament dispensing applications.

The reservoir 22 and outlet 24 preferably are arranged in a conventional manner, with the actuator 26 applying pressure on the contents of the reservoir 22 to cause the medicament to dispense through the outlet 24. More specifically, as the medicament is pressed by the actuator against the cap 25, the cap 25 is subjected to a force sufficient to expel the cap 25 from the capsule 20, thus allowing medicament to exit through the outlet 24. The controls 28 may take many forms and be of varying complexity, but preferably are arranged to control the actuator to dispense the medicament. In their various forms, some of which will be described in more detail below, the controls 28 may include a power source, such as a battery, an induction coil, or a capacitor, a receiver for receiving instructions to control the actuator to dispense the medicament, and a transmitter for transmitting information, such as an indication that a medicament has been delivered or information about a condition of the capsule.

The capsule may also include any number and manner of sensors (not shown). For example, the capsule may have sensors that detect environmental conditions, such as moisture, pH, and temperature. Such environmental sensors may be active in that they continuously report on the condition they are designed to monitor, but more preferably they are designed as "binary" sensors that change state upon some condition change. For example, the sensor may include a polymer that erodes in the presence of a specific condition, such as an elevated pH. This erosion causes a detectable short circuit, which detection may be used to turn on the electronics in the capsule. Using this type of sensor will conserve energy over the active sensors mentioned above. Sensors may also be included in or on the capsule, which confirm that the medicament is present in and/or has been discharged from the capsule.

In FIG. 2, the reservoir 22 is defined by a sidewall 21 of the capsule 20, the cap 25, and a movable plunger 32. The outlet 24 is an open end of the capsule 20. In other embodiments, the reservoir may be a bladder or lining disposed in the capsule. Moreover, the outlet 24 may be a smaller aperture or a plurality of apertures. The outlet 24 may open through the sidewall 21 in addition to or instead of through the capsule 20.

In this embodiment, the actuator 26 includes a spring 30 (shown coiled in FIG. 2), the plunger 32, and a filament 34. Before dispensing the medicament from the capsule 20, the spring 30 is retained in a retracted position, which is the position illustrated in solid lines in FIG. 2. The plunger 32 is disposed contacting the spring 30, between the spring 30 and the reservoir 22. The filament 34 is fixed to the plunger 32 and to the body of the capsule 20. According to this arrangement, the filament 34 fixes the position of the plunger 32 longitudinally along the capsule 20, and the plunger 32 acts against the force of the spring 30 to retain the spring in the compressed position.

A heating element 36 also is provided in the capsule of FIG. 2, proximate the filament 34. The filament 34 is a meltable filament that melts after being warmed by the heating element for a sufficient time and at a sufficient temperature. Without the connection provided by the filament 34, the plunger 32 can no longer retain the spring 30 in the compressed position, so the spring extends, driving the plunger 32 to an extended position (not shown in FIG. 2). The actuated plunger has sufficient force to press the medicament in the reservoir 22 against the cap 25 to expel the cap 25, thereby expressing the medicament through the outlet 24. The heating element 36 may be any conventional heater, although a preferred heating element is a resistive heater that is incorporated into the controls disposed in the capsule. The heater is preferably powered by an on-board power supply, which is also incorporated into the controls. In other embodiments, the filament could be broken by means other than melting. For example, the filament could be broken such as by cutting, dissolving, chemical reaction, or any other means. The invention is not limited to the illustrated filament. Any latch or stop capable of retaining the spring in the compressed position and which can subsequently be moved, removed, or destroyed to release the spring may be used.

Figure 5:
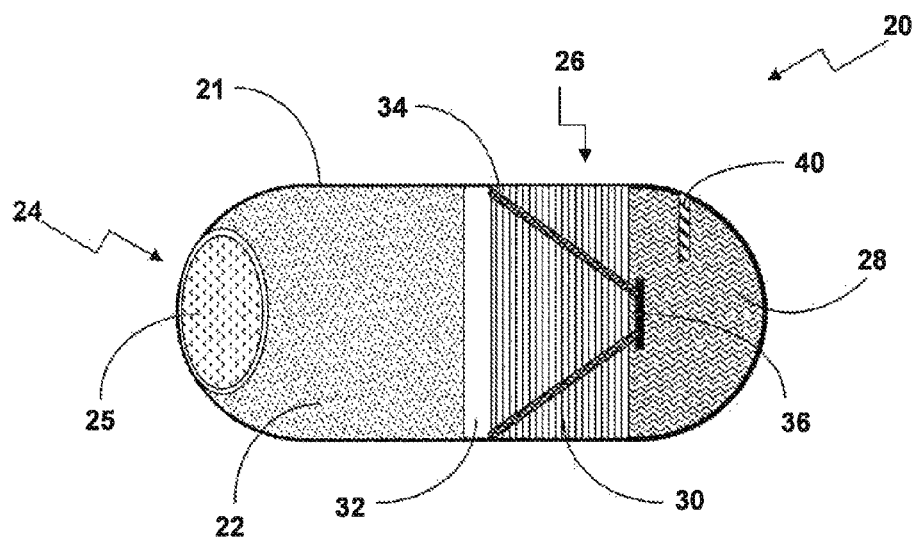
FIG. 5 is a section view of another embodiment of a capsule used in the system illustrated in FIG. 1.

In FIG. 5, a capsule substantially the same as the one illustrated in FIG. 2 is provided. Different from FIG. 2, however, is that FIG. 5 also schematically illustrates a switch 40. The switch 40 is provided to turn on the heater 36. In its simplest form, the switch completes a circuit to allow power to the heater 36.

Figures 6, 7:
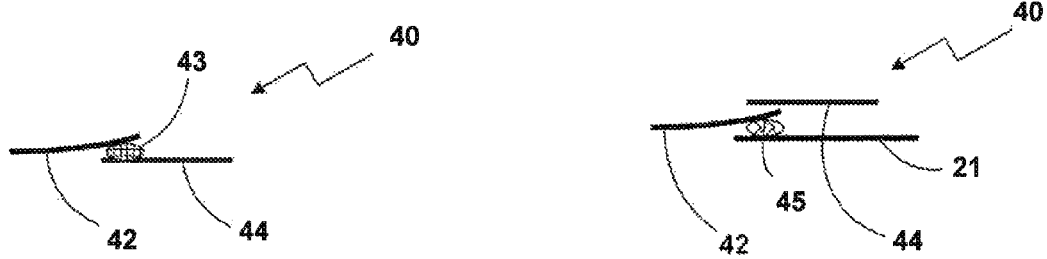
FIG. 6 is a schematic representation of a trigger illustrated in the capsule of FIG. 5.
FIG. 7 is a schematic representation of the trigger illustrated in the capsule of FIG. 5.

FIGS. 6 and 7 illustrate two embodiments of the switch 40. Each includes a flexible electrode 42 and a stationary electrode 44. When the two electrodes come into contact, a circuit is completed to provide power to, and thus turn on, the heater 36.

In FIG. 6, a dissolvable material 43 is provided between the flexible electrode 42 and the stationary electrode 44 to bias the flexible electrode 42 away from the stationary electrode. The material 43 is chosen to interact with a specific environmental condition within the body, e.g., a fluid of a specific pH. This interaction melts the material, and the flexible electrode 42 returns to an unbiased position, contacting the stationary electrode 44.

In FIG. 7, an expandable material 45 is provided between a wall 21 of the capsule and the flexible electrode 42. As the material 45 expands or swells, e.g., due to absorption of water or some other bodily fluid, the flexible electrode 42 is biased toward the stationary electrode 44, eventually resulting in contact of the two.

As will be appreciated by those having ordinary skill in the art, the capsule described herein is but one example of a relatively low-cost capsule effective to dispense a medicament at a desired time. Other capsules may also be used in the system of this disclosure, without departing from the disclosure's spirit and scope. In one alternative example, the capsule may not include a spring at all, but instead the cap or a similar covering is dissolved in a predetermined environment. Once the covering is dissolved, the medicament is unrestrained and diffuses or otherwise exits the capsule. In another embodiment, an actuator such as a compressed spring opens a valve allowing fluid from the environment to rush into the capsule. As a result of that rush, a secondary, more powerful actuator is actuated to force the medicament out of the capsule. In still another embodiment, the actuator may include a gas-forming or osmotic pressure engine that acts to push the medicament from the capsule. Moreover, although a mechanical trigger is illustrated in FIGS. 6 and 7, a timer may instead be used to trigger an activation of the heater.

As noted above, the capsule 20 is used as part of a medicament dispensing system 10, which also includes the external device 50. In a preferred embodiment, the capsule 20 is simple in construction and operation, and thus lower in cost, but the system 10 is very comprehensive. Accordingly, the external device 50 is configured to accomplish much of the functionality of the system, other than actual dispensing.

Figure 3:
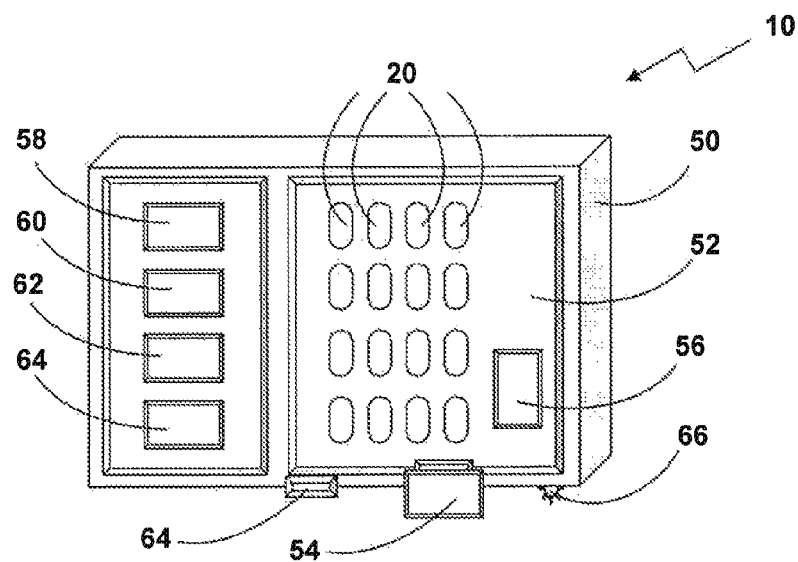
FIG. 3 is a schematic plan view of an external unit used in the system illustrated in FIG. 1.

As illustrated in the schematic top view of FIG. 3, the external device 50 includes a receptacle 52 that is sized and configured to store a plurality of the capsules 20. The capsules 20 may be provided in a unique package, such as a cartridge, for ready insertion into the receptacle 52, but the manner of retaining the capsules 20 in the receptacle is not limited. The external device 50 also includes an access opening 54 through which the user accesses the capsules 20 stored in the external device 50. The access opening preferably allows the user access to less than all of the capsules 20, and more preferably allows access only to the capsule or capsules that are to be administered at a given time. Thus, the external device 50 also acts as a dispenser of the capsules 20, similar to a conventional vending machine. Although not illustrated, suitable mechanical and electronic components may be included and/or required to achieve this dispensing feature. Such features may be similar to those found in conventional pill dispensing features, such as the PHILIPS® Medication Dispensing Service.

The external device 50 preferably also includes a capsule activator 56. The capsule activator 56 renders each capsule capable of dispensing medicament. That is, at the time of insertion into the external device 50, each capsule contains an amount of medicament, but is passive and thus unable to dispense the medicament. Put another way, the passive capsule locks the medicament inside and will not normally dispense the medicament until it is unlocked. Thus, upon being placed in the receptacle 52, the capsule is in a passive, nondispensed state. The capsule activator 56 changes the capsule to an active, non-dispensed state. In one presently preferred embodiment, the capsule activator is a charger that charges a power source on the capsule. For example, the capsule activator may inductively charge an induction coil or induction bank or charge a capacitor contained in the capsule. In another embodiment, the capsule activator may "wake up" or "power on" the capsule's power supply and/or electronics, such as by activating a switch on the capsule. In still another embodiment, the capsule activator charges the actuator, such as by pre-loading a spring. Other means of activating the capsules may also be contemplated. As will be appreciated, the activation feature of this disclosure has other benefits, as well. For example, if a user takes a capsule that is not activated, it will not dispense its contents, because those contents are locked inside. Controlled activation will prevent accidental overdoses, and could help curb narcotic abuse.

In one embodiment, the capsule activator 56 is integrated with the dispensing function of the external unit. For example, the capsule activator 56 is arranged proximate the access opening 54 such that the capsule is activated at the time the capsule is accessible to the user. The capsule activator may be provided in the form of a port or cradle into which a to-be-dispensed pill is placed for activation, and this port or cradle can be arranged at the access opening 54. In another embodiment, the activation port is upstream of the access opening 54. For example, an activation port serving as the capsule activator 56 may be inside the external device 50 where it activates the capsule prior to the pill being presented to the user at the access opening 54.

In still another embodiment of the invention, the capsule activator 56 may operate separately from the dispensing function. For example, a capsule may be dispensed to a user via the access opening 54, at which time the user places the capsule in the capsule activator 56. In this embodiment, visual, audible, or other indicia may be provided in connection with the capsule activator 56, to alert the user that the capsule is activated.

The external unit 50 allows for controlled dispensing and activation of capsules. To this end, the external unit 50 preferably includes a programmable memory 58 for storing a medicament administration profile. This profile provides the schedule that dictates when the capsules are to be activated and/or dispensed. The profile may be determined based on the drug, characteristics of the user, or some combination of the two. In preferred embodiments, the medicament administration profile is uploaded to the external unit, e.g., by a computer interface, the user, the medicament administrator, the prescribing doctor, a pharmacist, or the drug manufacturer/packager. When an interface is provided, the profile may be updated as prescriptions or conditions change. In other embodiments, the dispenser may be pre-programmed with the administration profile, and unchangeable by the user.

The external unit preferably also includes a clock 60. Most medicament administration profiles include a frequency of drug administration. The clock 60 is used to time dispensing and/or activation based on the administration profiles. The clock also may be used to establish a release time for the medicament. For example, the clock 60 may be used to determine an elapsed time after activation or after ingestion, which elapsed time could be predetermined and used to instruct release of the medicament from the activated capsule, for example by activating the heater of the capsule of FIG. 2.

The external unit 50 may also include a receiver 62 and a transmitter 64. The receiver 62 may be of any conventional arrangement, including but not limited a wired or a wireless receiver. In one embodiment, the receiver is configured to receive the medicament administration profile. The receiver also may receive information from an activated capsule, including but not limited to, information relating to a position of the capsule, confirmation that the capsule has dispensed its medicament, and information that the capsule has been ingested. Information received by the receiver may be stored by the external unit 50, such as in memory (not shown).

The transmitter 64 may be used to transmit instructions to an activated capsule to release the stored medicament. The transmitter 64 also may be used to transfer any information stored on the external unit, for example, to a caregiver or technician, such that stored information can be reviewed for diagnostic purposes.

The external unit 50 preferably also includes some number of user interfaces and/or user indicators. In the illustrated embodiment, the external unit 50 includes a light 66 as a visible indicator. The light 66 indicates when a medicament is to be administered. Thus, when the release profile, in conjunction with the clock, determines that a medicament is to be administered, the light 66 will illuminate. Other visual indicators, such as digital displays, touch screen displays, and the like, may also or alternatively be used. Moreover, the indicator is not limited to a visual indicator. An audible alarm may also or alternatively be included in the external unit 50.

While the inventors contemplate that a capsule may be dispensed and/or activated when the user receives the indication that the medicament is to be administered, in some embodiments, the user will first acknowledge that the indication has been administered. To this end, a dispense button 68 is provided on the external display. The user pushes the dispense button 68 upon receiving an indication that it is time to administer the medicament and the unit dispenses the capsule. As described above, activation may also occur at the time of dispensing.

As just described, a preferred system according to the disclosure includes two components, namely, a capsule and an external unit. The disclosure is not limited to this arrangement. The external unit may consist of more than one component. For instance, when the capsule has one or more of a transmitter and a receiver, the user may be required to remain in close proximity with the external unit, to allow for communication. So the user is not tethered to one location, he may be provided with a wearable module that, among other features, facilitates communication with the capsule. A separate, stationary module would then be provided, to perform other functions of the external unit described above, such as dispensing and activation. The features and functions of the external unit may be parsed among any number of modules, as design dictates.

Figure 4:
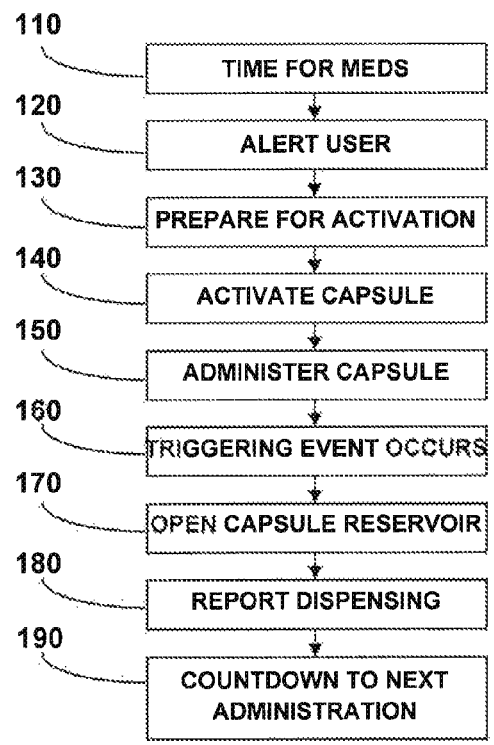
FIG. 4 is a flow chart illustrating a medicament delivery method according to an embodiment of the invention.

Methods of administering a medicament using the system 10 described above now will be described, with particular reference to the flow chart of FIG. 4.

In step 110, the external unit determines that it is time to administer a capsule. This is done using information from the aforementioned and described medicament administration profile. This determination will likely also include inputs from the clock or other sources.

In step 120, the user is alerted to the fact that it is time to administer the medicament. In the embodiment discussed above, the user is notified when a light on the external unit 50 is turned on. Alternatively, the user could be notified by an audible indicator. In still other embodiments, the external device could notify the user by sending a message such as a text or e-mail message to a device carried by the user.

In step 130, the capsule is prepared for activation. For example, it may be placed in a port or cradle that will act as or in connection with the capsule activator described above. In a preferred embodiment, the capsule is automatically placed, i.e., by a mechanism in the external unit, in to the port or cradle. In other embodiments, step 130 may include presenting a passive capsule to the user, who manually transfers the capsule to the capsule activator or who manually activates the capsule, e.g., by activating a switch on the capsule.

In step 140, the capsule is activated. As will be appreciated, prior to this step, the capsule is preferably passive or dormant. That is, it will not dispense the medicament absent some unauthorized external force that operably destroys the capsule. Only after the capsule is activated, in this step 140, will the capsule be prepared to dispense the medicament as intended. In some embodiments the capsule may be activated by being coupled to an energy source, with energy from the source being stored in the capsule for functional operation. For example, the capsule may be plugged in to charge a battery or capacitor stored therein, or the battery or capacitor may be charged inductively. The activation may also be done by changing an electrical or mechanical switch, such as from an "off" to an "on" position In step 150, the capsule is administered to the user. In a preferred embodiment the user ingests the capsule, but other means of administering the capsule, such as by rectal or vaginal insertion, are also contemplated.

In step 160, the capsule receives information that a triggering event has occurred. The triggering event may be any number of events, including but not limited to activation of the capsule (step 140) or administration of the capsule (step 150). Administration of the capsule may be detected by including a moisture-detecting sensor on the capsule to determine when the capsule enters the relatively moist environment of the user's alimentary canal. The user may also manually verify that he administered the capsule, such as by pressing a button on the external unit. In another embodiment, the capsule may include a pH sensor, and detection of a certain, predetermined pH value will be the triggering event.

After detection of the triggering event, in step 170 the capsule dispenses the medicament such as by opening the capsule's reservoir, as discussed above. Dispensing may occur immediately upon the triggering event or it may happen at some predetermined time after the triggering event.

In step 180, the capsule reports that the medicament has been dispensed. It may do this by sending a signal, e.g., by RF transmission, to the external unit. In other embodiments, a state of the capsule may be changed when the medicament is released, and the user may note this change in state when the capsule is passed. The indication that the medicament has been dispensed may be a binary indication, or it may be more in depth, depending upon the sensing capabilities of the capsule and the external unit. For example, the indication that the medicament has been dispensed may include a location of dispensing, a time of dispensing, and/or any other pertinent information. This step 180 may not be required at all in some embodiments, for example, if there is sufficient confidence that an administered capsule will function properly.

In step 190, the external unit starts a timer that will establish when the next administration of the medicament is to take place. The timer may be started when administration of the medicament is determined, in step 180. In other embodiments, the timer may be started when a capsule is dispensed, when a capsule is activated, when a capsule is ingested, or upon the triggering event occurring in step 170.

The methods just described, and variations thereof, are effective at accurately administering medicaments to a user according to a predetermined schedule. The improved methods inhibit improper administration of medicaments. Moreover, each of the steps is preferably stored in a memory of the external unit, thus allowing a user or caregiver the ability to track and confirm administration of the medicament. This knowledge is particularly valuable when coupled with other information about the user, because it allows for accurate diagnosis and indication of treatment regiments.

Moreover, although presently preferred embodiments of the disclosure have the bulk of the intelligence of the system in the external unit, such is not required. In one alternative embodiment, the capsule may include a memory storing the administration schedule, such that it need not receive instruction from the external unit to dispense the medicament. Similarly, a small processor may be provided in each capsule, such that the capsule detects the triggering event and as a direct result of the triggering event, or after some elapsed time calculated by a clock in the capsule, releases the medicament.

The foregoing embodiments of the present invention are provided as exemplary embodiments and are presently best modes for carrying out the invention. Modifications of these embodiments will be readily apparent to those of ordinary skill in the art. The invention is not intended to be limited by the foregoing embodiments, but instead is intended to be limited only by the appended claims.

The invention claimed is:

1. A system for administering a medicament comprising:
a plurality of capsules, each capsule comprising:
a reservoir containing a medicament, and an outlet through which the medicament is released from the reservoir,
a switch selectively activatable to change the capsule between a passive state and an active state,
each capsule being configurable in the active state in which a triggering event results in release of the medicament from the reservoir and the passive state in which the triggering event does not result in release of the medicament from the reservoir; and
a capsule dispenser comprising:
a receptacle releasably containing the plurality of capsules each of the plurality of capsules being in the passive state in the receptacle,
a capsule activator configured to activate the switch of the capsule by changing the capsule from the passive state to the active state, and an access opening through which the user accesses at least one of the plurality of capsules, wherein the at least one of the plurality of capsules is activated by the capsule activator prior to the capsule being placed at the access opening or while located at the access opening.

2. The system of claim 1, each of the plurality of capsules further comprising an actuator for expelling the medicament through the outlet.

3. The system of claim 2, each of the plurality of capsules further comprising a power source.

4. The system of claim 3, wherein the capsule activator comprises a charger for charging the power source.

5. The system of claim 2, wherein the actuator comprises a spring.

6. The system of claim 5, wherein the spring is maintained in a compressed state until the triggering event and moves to an extended position after the triggering event to release the medicament.

7. The system of claim 6, further comprising a destructible filament maintaining the spring in the compressed state prior to the triggering event.

8. The system of claim 6, wherein the triggering event comprises at least one of a sensed condition at the capsule or expiration of a predetermined time period.

9. The system of claim 2, wherein the actuator is a movable covering disposed over the outlet until the triggering event, at which time the covering is removed from the outlet.

10. The system of claim 2, wherein each of the plurality of capsules further comprises an actuator control switch for activating the actuator after detecting the triggering event.

11. The system of claim 10, wherein the actuator control switch comprises a fixed electrode and a flexible electrode movable relative to the fixed electrode.

12. The system of claim 2, wherein the actuator expels the medicament through the outlet after the triggering event.

13. The system of claim 12, wherein the triggering event is at least one of a sensed condition at the capsule, a change in state of the capsule, expiration of a predetermined time period, and activation of a switch.

14. The system of claim 1, each of the plurality of capsules further comprising a sensor for sensing a condition in the user.

15. The system of claim 1, the capsule dispenser and the capsule activator being integrated into a single unit.

16. The system of claim 15, wherein the capsule activator comprises an activation port positioned to receive a dispensed capsule and adapted to activate the capsule.

17. The system of claim 1, the capsule dispenser comprising a controller programmed to dispense capsules according to a dosing schedule.

18. The system of claim 1, further comprising a transmitter in the capsule for transmitting information to an external unit.

19. The system of claim 18, wherein the transmitted information is measured by a sensor at the capsule.

20. A method of administering a medicament to a subject, comprising:
storing a plurality of capsules in a storage unit in a passive state, each of the capsules including a reservoir containing the medicament and an outlet through which the medicament is released from the reservoir, each of the capsules comprising a switch selectively activatable to change the capsule between the passive state and an active state, and each capsule being configurable in the active state in which a triggering event results in release of the medicament from the reservoir and the passive state in which the triggering event does not result in release of the medicament from the reservoir;
activating a first capsule by changing the first capsule from the passive state to the active state by activating the switch, and
placing the activated first capsule at an access opening of the storage unit.

21. The method of claim 20, further comprising triggering release of the medicament.

22. The method of claim 21, wherein the triggering comprises sensing a condition at the first capsule.

23. The method of claim 21, wherein the triggering comprises expiration of a predetermined time period.

24. The method of claim 23, wherein the predetermined time period commences at one of activating the first capsule or administering the first capsule to the user.

25. The method of claim 20, further comprising dispensing the medicament according to a dosing schedule.

26. The method of claim 20 wherein the activating the first capsule step-comprises charging a power source on the first capsule.

27. The method of claim 20 further comprising monitoring release of the medicament from the capsule.

* * * * *